(12) United States Patent
Swenson et al.

(10) Patent No.: US 11,452,878 B2
(45) Date of Patent: Sep. 27, 2022

(54) IN-PACKAGE IMD CONFIGURATION MANAGEMENT, SELF-TEST, AND PROGRAMMING SUPPORT SYSTEM FOR ACOUSTIC COMMUNICATION ENABLED IMPLANTS

(71) Applicant: BIOTRONIK SE & Co. KG, Berlin (DE)

(72) Inventors: Kurt Swenson, Dayton, OR (US); Brian M. Taff, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 96 days.

(21) Appl. No.: 16/811,189

(22) Filed: Mar. 6, 2020

(65) Prior Publication Data

US 2020/0316390 A1    Oct. 8, 2020

Related U.S. Application Data

(60) Provisional application No. 62/829,658, filed on Apr. 5, 2019.

(51) Int. Cl.
| | | |
|---|---|---|
| *A61N 1/37* | (2006.01) | |
| *A61N 1/372* | (2006.01) | |
| *A61N 1/375* | (2006.01) | |

(52) U.S. Cl.
CPC ..... *A61N 1/37229* (2013.01); *A61N 1/37217* (2013.01); *A61N 1/37512* (2017.08); *A61N 1/3756* (2013.01); *A61N 2001/37294* (2013.01)

(58) Field of Classification Search
CPC .................. A61N 1/37217; A61N 2001/37294
See application file for complete search history.

(56) References Cited

U.S. PATENT DOCUMENTS 10,039,527 B2 *   8/2018  Pelissier ............... A61B 8/58
2006/0020300 A1 * 1/2006  Nghiem ............... A61B 50/30
                                                              607/60

(Continued)

FOREIGN PATENT DOCUMENTS

WO    20080130292 A1    10/2008
WO    20170116752 A1    7/2017

OTHER PUBLICATIONS

European Search Report and Annex to the European Search Report on European Patent Application No. EP 20 16 4466.3 dated Jun. 17, 2020 (7 pages).

(Continued)

*Primary Examiner* — Eric D. Bertram
(74) *Attorney, Agent, or Firm* — Buchanan Ingersoll & Rooney PC

(57) ABSTRACT

The present disclosure relates to a system, comprising: an implantable medical device, wherein the implantable medical device comprises an ultrasound transducer configured to receive an ultrasound wave, a packaging, wherein the packaging encloses an internal space, wherein the implantable medical device is arranged in the internal space, and a device mount arranged in the internal space, wherein the implantable medical device is fastened to the device mount in a releasable fashion, and wherein the device mount contacts an inner side of a portion of the packaging and forms an acoustic coupler configured to pass an ultrasound wave applied to an outer side of the portion of the packaging to the ultrasound transducer of the implantable medical device.

13 Claims, 6 Drawing Sheets

(56) References Cited

U.S. PATENT DOCUMENTS

| | | | |
|---|---|---|---|
| 2007/0119741 A1* | 5/2007 | Wenger | A61N 1/372 206/438 |
| 2007/0123947 A1* | 5/2007 | Wenger | A61N 1/372 607/32 |
| 2007/0162090 A1* | 7/2007 | Penner | A61N 1/37235 607/60 |
| 2011/0041613 A1* | 2/2011 | Tran | A61N 1/372 73/632 |

OTHER PUBLICATIONS

European Search Report and Annex to the European Search Report on European Patent Application No. EP 19 17 5925.7, dated Oct. 25, 2019 (7 pages).

* cited by examiner

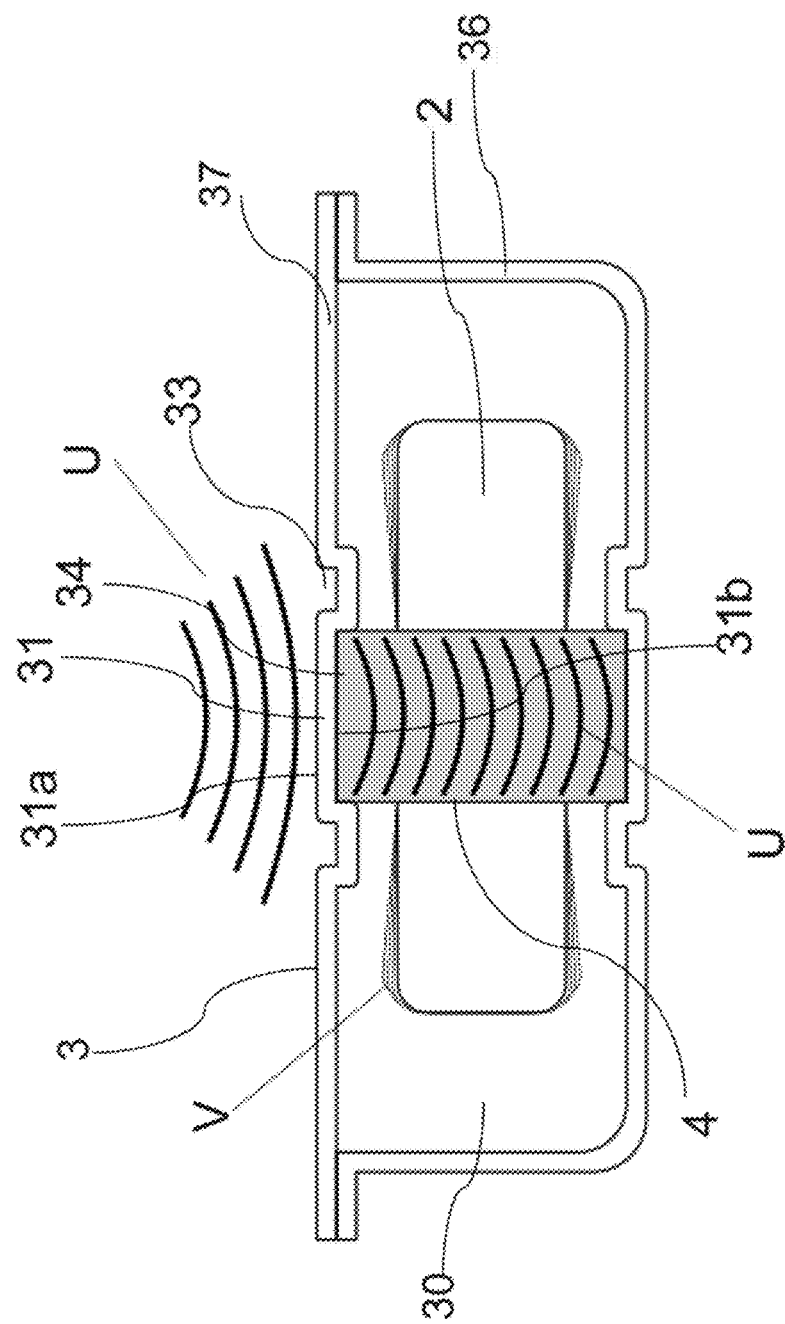

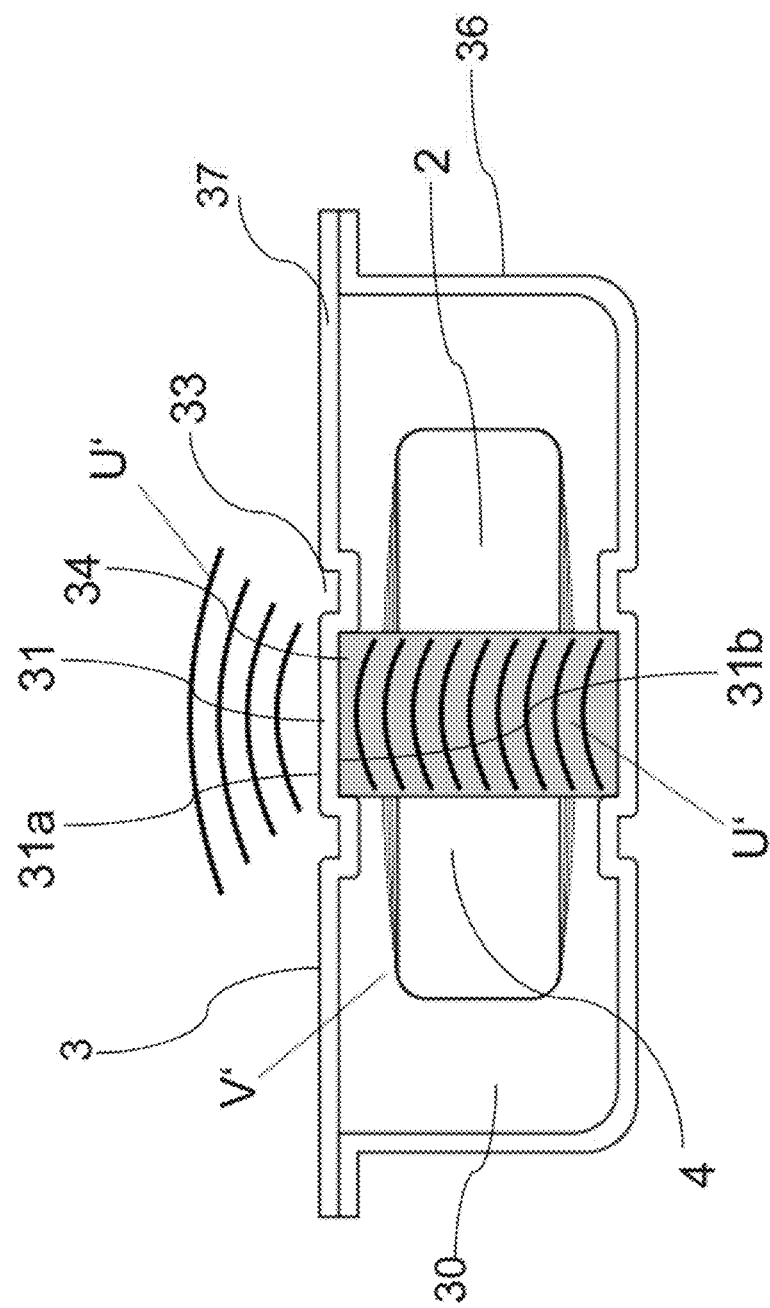

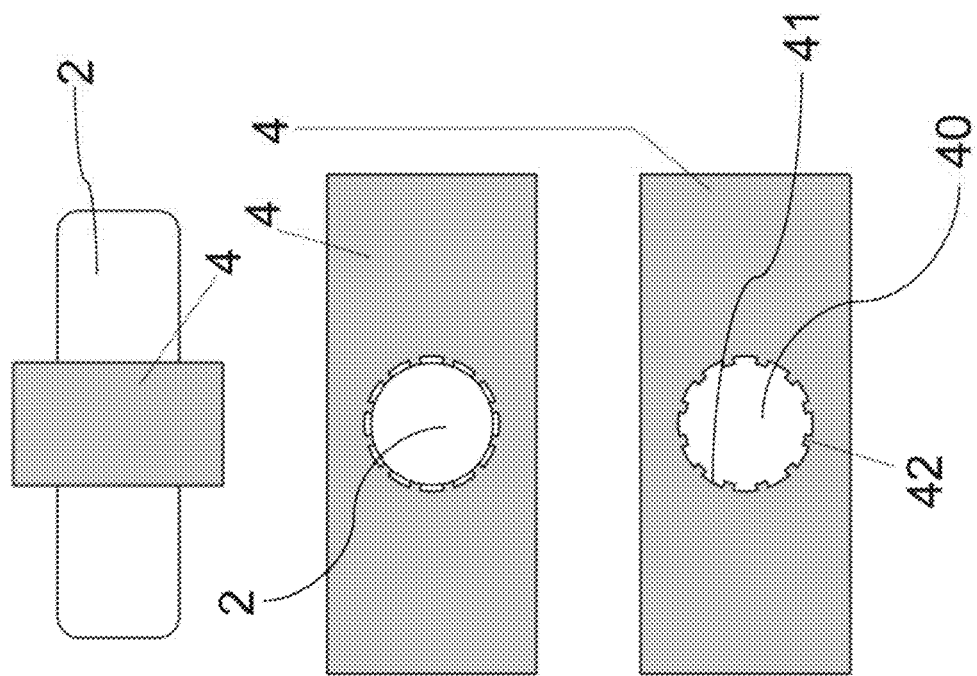

IN-PACKAGE IMD CONFIGURATION MANAGEMENT, SELF-TEST, AND PROGRAMMING SUPPORT SYSTEM FOR ACOUSTIC COMMUNICATION ENABLED IMPLANTS

CROSS-REFERENCE TO RELATED APPLICATIONS

This patent application claims the benefit of, and priority to, co-pending U.S. Provisional Patent Application No. 62/829,658, filed on Apr. 5, 2019, which is hereby incorporated by reference in its entirety.

TECHNICAL FIELD

The present invention relates to a system comprising an implantable medical device arranged in packaging. Furthermore, the present invention relates to a method involving such a system.

BACKGROUND

Usually, a programming device or a similar device is used at the factory level to query an implantable medical device to make sure it is functioning properly before transport/shipping. Similarly, a clinician can interrogate the implantable medical device with a programming device before removing it from the sterile packaging in order to ensure that the device is working normally and can communicate properly.

Some implantable medical devices, such as e.g. leadless components that are intended to be implanted directly in the heart (particularly intracardiac devices that are implanted in the atrium), may only be designed to communicate with another device that is also implanted, either in the heart or near it. One means of communicating between such components is by sending modulated ultrasonic waves through the intervening tissue. This mode of communicating does not work well through air and is therefore incompatible with external user interface devices like a programming device based e.g. on near-field inductive communication. This makes it difficult to tell if the implantable medical device is working prior to shipping or implantation, especially since the implantable medical device is often put in an inactive shipping state at the factory.

Particularly, International Publication No. WO 2017/116752 discloses systems and methods for wirelessly powering and/or communicating with a sterile-packed electronic device without removing the electronic device from its sterile packaging and while maintaining the sterility of the electronic device.

U.S. Publication No. 2011/41613 describes systems and methods of acoustically interrogating a packaged medical implant such as an implantable sensor. An illustrative system includes a sterilizable package including a package tray and a cover, a sensor module disposed within the package, and an acoustic coupling member disposed within an interior space of the package tray. An external interrogator located outside of the sealed package can be used to acoustically communicate with the sensor module.

Based on the above, it is an objective to provide a means allowing an improved communication with the implantable medical device in the packaged state, particularly for enabling device configuration support, self-tests, particularly including display of self-test results, and device programming.

The present invention is directed at overcoming one or more of the above-mentioned problems.

SUMMARY

At least the above problem(s) is solved by a system having the features of claim 1. Further embodiments of the system are stated in the sub claims and are described below.

A system is disclosed, comprising:
an implantable medical device, wherein the implantable medical device comprises an ultrasound transducer configured to receive an ultrasound wave,
a packaging, wherein the packaging encloses an internal space, wherein the implantable medical device is arranged in the internal space, particularly in a hermetically sealed and preferably sterile fashion, and
a device mount arranged in the internal space and particularly fixed with respect to the packaging, wherein the implantable medical device is fastened to the device mount in a releasable fashion, and wherein the device mount contacts an inner side of a portion of the packaging and forms an acoustic coupler configured to pass an ultrasound wave coupled into an outer side of the portion of the packaging to the ultrasound transducer of the implantable medical device.

Furthermore, the system comprises an external device, particularly a mobile hand-held device, arranged outside the internal space of the packaging, wherein the external device is configured to generate an ultrasound wave, and wherein the external device is configured to contact the outer side of the portion of the packaging so that said portion of the packaging butts against the device mount as well as against the external device and an ultrasound wave generated by the external device can be passed from the external device to the ultrasound transducer of the implantable medical device via said portion of the packaging and the device mount that serves as an acoustic coupler.

Besides the external device, the system comprises a programming device (e.g. in form of a programming device with a programming wand) that preferably comprises a user interface and is configured to generate and send a command signal to the external device (e.g. using inductive communication via the wand or radio communication) in case the external device receives a corresponding input by a user via the user interface of the programming device.

A programming device allows to set and adjust parameters of an implantable medical device, like an implantable intracardiac pacemaker or an implantable sensor, as well as providing additional functions, such as creating reports for the implantable medical device. In addition, the programming device can be configured to generate and send a command signal to the external device. A programming wand (wand) is used to communicate data between a programming device and an implantable medical device or an external device as mentioned above. The programming device and the wand can be connected using a wired connection (e.g. a USB-connection using a USB cable) or a wireless connection (e.g. a WLAN or a Bluetooth connection).

According to an embodiment of the system, the device mount comprises a through-opening, wherein the implantable medical device is inserted in the trough-opening to fasten the implantable medical device to the device mount.

According to a preferred embodiment, the implantable medical device tightly butts against a circumferential inner side of the through-opening. Further, particularly, the implantable medical device may protrude out of the through-opening of the device mount with two opposing ends of the implantable medical device. Thus, the device mount preferably encompasses a cross section of the implantable medical device.

According to a further embodiment of the system, the inner side of the through-opening comprises a plurality of protrusions pressing against the implantable medical device so that the latter is fastened to the device mount through a press fit.

Further, according to an embodiment of the system, the packaging comprises an inner recess facing the internal space of packaging, which inner recess is formed on an inner side of the packaging, wherein the device mount preferably engages with the inner recess in a form fitting manner, e.g., so as to help avoid movement of the implantable medical device arranged in the internal space of the packaging when the packaging is moved.

According to a further embodiment of the system, the packaging comprises a container and a removable lid connected to the container, wherein the inner recess is formed in the lid.

According to a further embodiment of the system, the packaging comprises an outer recess formed on an outer side of the packaging, wherein the outer recess is configured to receive a portion of the external device so as to align the external device with respect to the device mount.

Here, in an embodiment, the external device is configured to receive the command signal and to convert the command signal into an ultrasound wave and to send the ultrasound wave via the device mount to the implantable medical device to trigger the implantable medical device to perform a task. In an embodiment, the command signal is provided in form of an inductive communication or a radio communication.

Further, in an alternative embodiment, particularly when using a programming device, see above, the implantable medical device is configured to generate a response signal in form of an ultrasound wave after having performed the task and to send the response signal via the device mount to the external device, wherein the external device is in turn configured to convert the response signal into a converted signal and forward the converted signal to the programming device, wherein the programming device is configured to display reception of the converted signal and/or an information contained in the converted signal via the user interface of the programming device. Particularly, the converted signal can be based on a non-propagating magnetic field generated by a communication coil of the external device and received by a communication coil of the programming device. Alternatively, the converted signal can also be a radio signal (i.e. an electromagnetic wave).

Preferably, according to an embodiment, said task described above is a self-test of the implantable medical device, wherein particularly said information is a result of the self-test.

Furthermore, according to a preferred embodiment, the implantable medical device is an implantable intracardiac pacemaker, e.g. a pacemaker comprising a housing enclosing a pulse generator configured to generate electric pacing pulses to be applied to the heart of the patient, wherein the housing itself is configured to be implanted into the heart of the patient (e.g. into an atrium of the heart). Particularly, in case of such a pacemaker, a pacing electrode via which the pacing pulses are applied to the heart of the patient, is arranged on the housing of the pacemaker (e.g. at a distal end of the housing) and not on a flexible electrode lead connected to the housing via a header as in the case of a usual cardiac pacemaker. Such a pacemaker is therefore also denoted as leadless pacemaker. Particularly, the intracardiac pacemaker is configured to communicate via ultrasound communication/waves with another pacemaker (e.g. another intracardiac pacemaker) that may be implanted into the ventricle of the heart of the patient so as to provide dual chamber pacing.

According to yet another aspect, a method for sending a signal to an implantable medical device using a system according to the present disclosure is provided, wherein the method comprises the steps of:

placing an external device on the portion of the packaging and applying an ultrasound wave to said portion of the packaging such that the ultrasound wave is passed via the device mount to the implantable medical device enclosed by the packaging.

According to a further embodiment, the method comprises the further step of generating a response signal in the form of an ultrasound wave with the implantable medical device and passing the ultrasound wave/response signal to the external device via the device mount.

The communication using ultrasound waves generated by the external device can be used to program the implantable medical device arranged in the internal space of the closed packaging, to trigger the implantable medical device to perform a self-test while still being arranged in the internal space of the closed packaging, or to activate and/or deactivate the implantable medical device arranged in the internal space of the closed packaging.

Additional features, aspects, objects, advantages, and possible applications of the present invention will become apparent from a study of the exemplary embodiments and examples described below, in combination with the Figures, and the appended claims.

DESCRIPTION OF THE DRAWINGS

In the following, embodiments and further features and advantages are described with reference to the Figures, wherein:

FIG. 4 shows passing of an ultrasound wave via the device mount to the packaged implantable medical device;

FIG. 5 shows passing of an ultrasound wave from the implantable medical device via the device mount to an exterior of the packaging; and FIGS. 6A-6C show different views of the device mount and implantable medical device, wherein FIG. 6A shows a top view of the device mount and implantable medical device, FIG. 6B shows a side view of the device mount and implantable medical device, and FIG. 6C shows a side view of the device mount without the implantable medical device.

DETAILED DESCRIPTION

Figure 1:
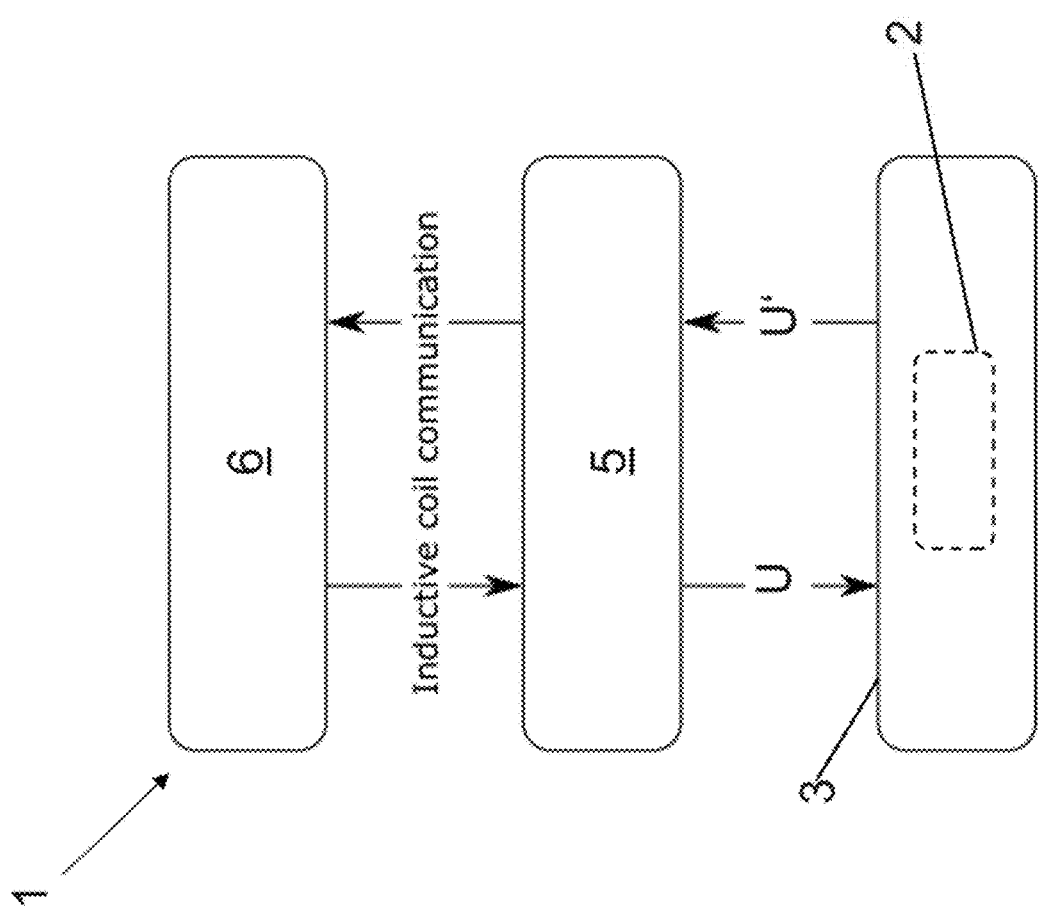
FIG. 1 shows a schematic illustration of an embodiment of the system/method.

FIG. 1 shows a schematic illustration of an embodiment of a system 1. As shown in FIG. 1, the system comprises a packaging 3 enclosing an implantable medical device (IMD)

2. The system 1 further comprises an external device 5 that is preferably configured to communicate with the IMD 2 via ultrasound waves U, U'.

Particularly, the sterile packaging 3 used to store and ship the IMD 2 before its use is designed to provide an acoustic path from the IMD's housing to an outside of the packaging 3. For this, the reusable external device 5 that can be placed in physical contact with the outside of the packaging 3 such that ultrasonic communications from/to the IMD 2 can allow this external device 5 to communicate with the IMD 2 while it is still in the sterile packaging 3.

According to an embodiment, the external device 5 can be designed to communicate with a (e.g. standard) programming device or wand 6 using inductive communication. For this, the programming device 6 and the external device 5 can each comprise a communication coil. This allows the programming device 6 to trigger a self-test of the IMD 2 and report the results to the clinician before the IMD 2 is implanted. It also allows a similar inductive communications-based programming device 6 to be used to verify that the IMD 2 is working properly and configured properly before shipment from the factory. In another embodiment of the envisioned system 1, the external device 5 (also denoted as middle device or bridge device in case a programming device 6 is used) can be used in a stand-alone mode to trigger the self-test when the user pushes a button 51 of the external device and to display the results using at least one LED 52 or some other form of user interface.

In order to provide a sufficient coupling of ultrasound waves to the IMD 2 (or from the IMD 2 to the external device 5), the system 1 preferably comprises a device mount 4 having good ultrasonic conduction properties. The device mount 4 thus also serves as an acoustic coupler. A suitable material for the device mount is Poly(methyl methacrylate) (PMMA). Preferably, as shown e.g. in FIG. 2, the mount 4 is designed such that when the packaging 3 is sealed, the device mount 4 remains in tight contact with the packaging 3 that separates the internal space 30 of the packaging 3 from the outside world.

Figure 2:
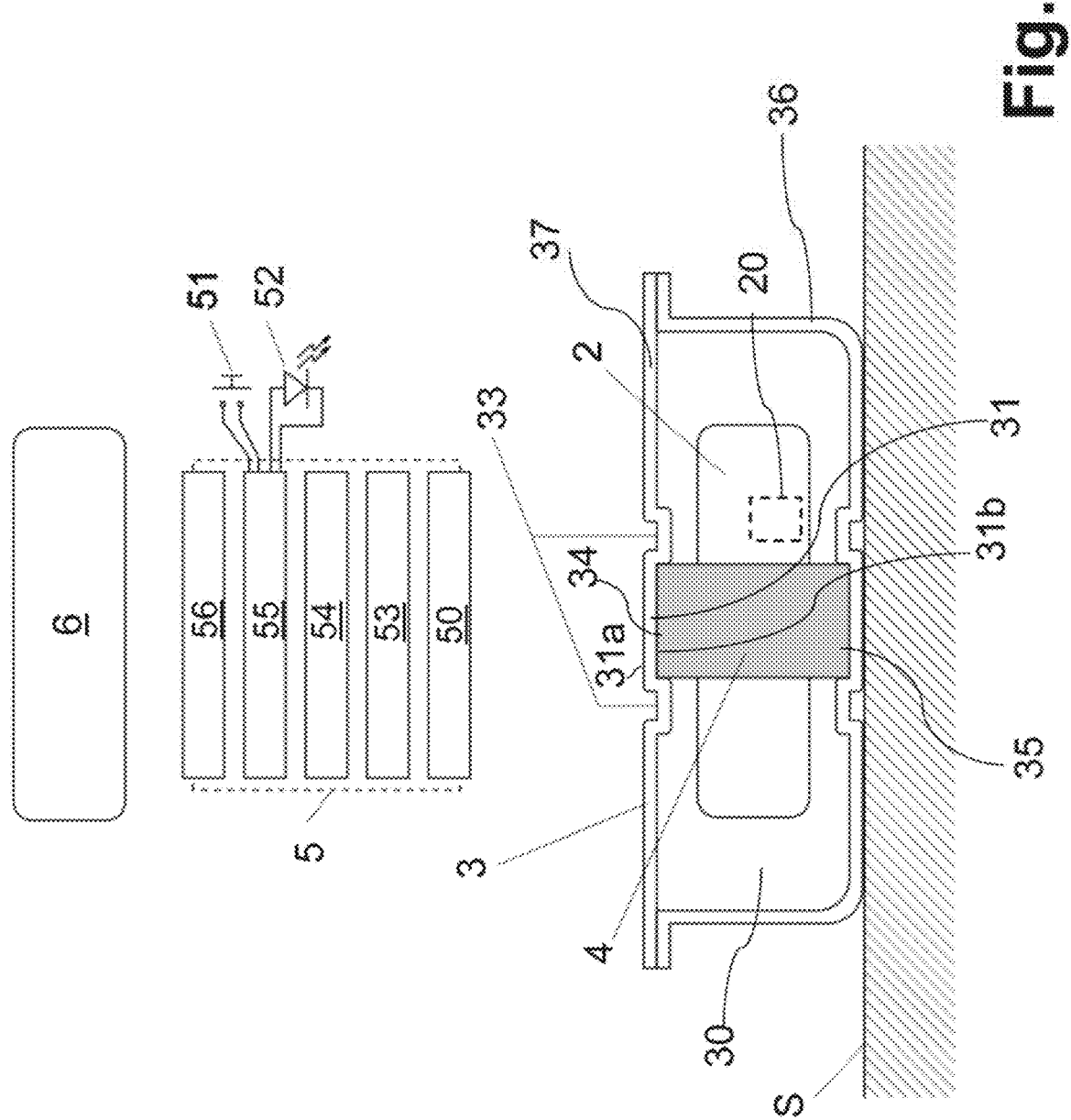
FIG. 2 shows a schematical cross-sectional view of an embodiment of the system.

FIG. 2 shows an embodiment of the system 1, wherein the packaging 3 enclosing the internal space 30 of the packaging 3 comprises a portion 31 that comprises an inner side 31b facing the internal space 30 and an outer side 31b facing towards the exterior of the packaging 3, wherein the external device 5 is configured to butt against said outer side 31a of the portion 31 of the packaging 3. Particularly, for aligning the external device 5 with the device mount 4, the outer side 31a can comprise at least one outer recess 33 which the external device 5 can engage when it is properly aligned with the device mount 4. On the other side, the inner side 31b of said portion 31 of the packaging 3 tightly butts against the device mount 4, so that ultrasound waves U can be coupled into the IMD 2 via said portion 31 and the device mount 4.

Furthermore, an inner recess 34 can be present on the inner side 31b of said portion 30 of the packaging 3 which is engaged by the device mount 4 to avoid lateral movement of the device mount 4 in the internal space 30 of the packaging 3. Particularly, as shown in FIG. 2, the portion 31 can be formed by a removable lid 37 of the packaging 3 that is connected to a container 36 of the packaging 3. Particularly, also a bottom of the container 36 can comprise a recess 35 engaged by the device mount 4 for preventing lateral movement of the device mount 4.

Furthermore, as indicated in FIG. 2, the external or bridge device 5 can consist of, or include, a packaged electronic module, including a power source (battery or external power adapter) 53, a control logic 54, and an ultrasonic transducer/transceiver 50. It can optionally include an inductive communication coil 56 and transceiver capable of communicating with an (e.g. standard) IMD programming device 6. The logic 54 particularly includes circuitry or a microcontroller which implements the protocol to support bridging between the ultrasound and inductive communications signals. Such support enables both pre-implant configuration support management as well as installation of program settings in pre-implant states. It can also optionally include a user interface 55 that allows a clinician or factory technician to trigger sending commands to the IMD 2 to request that a self-test be run. Such support need not involve any programming device 6 and can strictly rely upon the in-package coupler (i.e. the device mount 4) and the external device ("bridge") 5. The results from the self-test, when returned by the IMD 2 at the completion of the self-test, can be displayed to the user, e.g. with LEDs 52 or similar user interface mechanisms of the external device 5.

Figure 3:
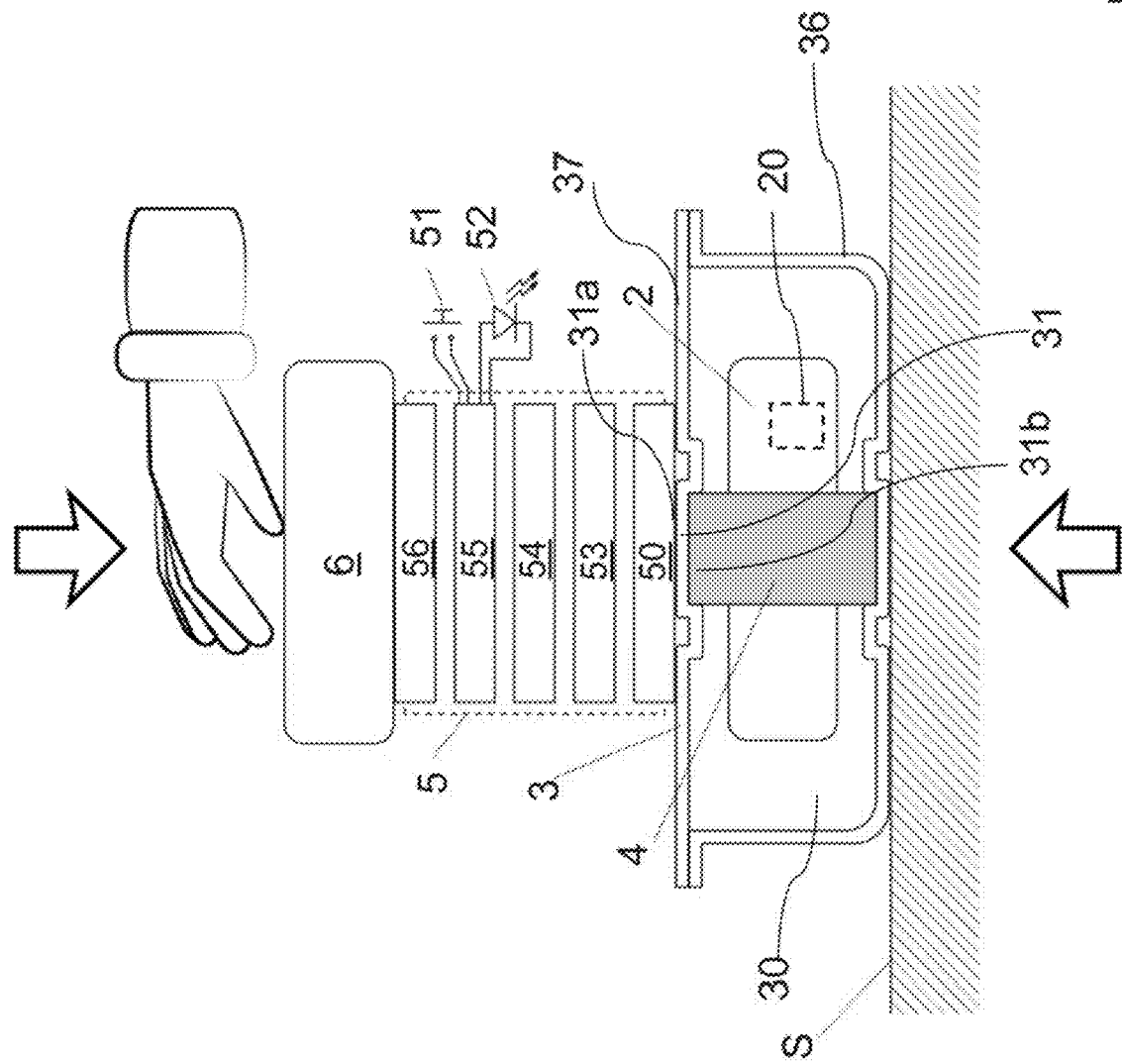
FIG. 3 shows holding of an external device against a packaging of an implantable medical device of the system in order to communicate with the implantable medical device using ultrasound signals.

Preferably, according to an embodiment, the system 1 is used as shown in FIG. 3. The external device 5 that may form the "bridge unit" is placed in physical contact with the packaged IMD 2, particularly with the outer side 31a of said portion 31 of the packaging 3, which has preferably been placed on a rigid work surface S. The programming device 6 is placed within proximity of the external device 5, or the standalone test button(s) 51/user interface 55 is/are operated to let the ultrasonic transducer 50 in the external device 5 cause a modulated ultrasound wave U to travel through the packaging 3 (e.g. through portion 31), the inner device mount 4 and into the housing of the IMD 2, where the IMD's ultrasonic transducer 20 preferably converts the ultrasound wave U into an electrical signal that is decoded by the IMD's 2 circuitry (see FIG. 4, wherein V indicates vibrations of the IMD 2 due to the ultrasound wave U). The IMD 2 preferably interprets the commands received in this way and performs the requested tasks. A response is formulated by the IMD 2 and converted into an electrical signal that drives the IMD's ultrasonic transducer 20. This causes a modulated ultrasound wave U' to travel through the device mount 4 and the packaging 3 (e.g. portion 31) into the transducer 50 of the external device 5 (cf. FIG. 5, wherein V' indicates vibrations of the IMD 2 due to the ultrasound wave U'), where it is converted to an electrical signal that is interpreted by the logic in the external device 5 and either passed on to the programming device 6 or displayed on a component of the user interface 55, e.g. LED 52 (cf. FIG. 3).

According to an embodiment of the system 1 shown in FIG. 6, the IMD 2 is retained in the packaging 3 using a pressure fit in the device mount 4. For this, the device mount 4 can comprise a through-opening 40 for receiving the IMD 2. The opening 40 comprises a circumferential inner side 41 forming protrusions 42 for pressing against the IMD 2 to realize said press fit when the IMD 2 extends through the opening 40.

When implanting the IMD 2, the sterile packaging 3 is opened and the IMD 2 and device mount 2 are released from the package 3. The IMD 2 is then removed from the device mount 4, e.g. by grasping the IMD 2 and pulling it out of the opening 40/away from the protrusions 42.

According to a preferred embodiment, the IMD 2 is an intracardiac (e.g. leadless) pacemaker. Here, also an implantation tool for implanting the IMD can be contained in the packaging 3. After removing the IMD 2 from the device mounting 4, the IMD 2 is inserted into the implantation tool to prepare it for the implantation process.

Due to the present invention, the implantable medical device 2 can be made smaller in an advantageous fashion since it does not have to contain a communications coil to allow communication in the packaged state. Instead, communication with the packaged IMD 2 is performed using ultrasound signals that can be transmitted via the device mount 4 that also serves as an acoustic coupler.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A system, comprising:
   an implantable medical device, wherein the implantable medical device comprises an ultrasound transducer configured to receive an ultrasound wave (U),
   a packaging, wherein the packaging encloses an internal space, wherein the implantable medical device is arranged in the internal space,
   a device mount arranged in the internal space, wherein the implantable medical device is fastened to, and held in place inside the packaging by, the device mount in a releasable fashion, and wherein the device mount contacts opposing inner sides of a portion of the packaging and forms an acoustic coupler configured to pass the ultrasound wave (U) applied to either opposing outer side of the portion of the packaging to the ultrasound transducer of the implantable medical device with the device mount in a first orientation,
   an external device, wherein the external device is configured to generate the ultrasound wave (U), and wherein the external device is configured to be held against either outer side of the portion of the packaging so that said portion of the packaging butts against the device mount as well as against the external device and the ultrasound wave (U) generated by the external device is transferable from the external device to the ultrasound transducer of the implantable medical device via said portion of the packaging and the device mount, and
   a programming device that comprises a user interface and is configured to generate and send a command signal to the external device in case the programming device receives a corresponding input by a user via the user interface of the programming device, wherein the external device is configured to convert the command signal into the ultrasound wave (U) and to send the ultrasound wave (U) via the device mount to the implantable medical device to trigger the implantable medical device to perform a task,
   wherein the packaging comprises outer recesses formed in outer opposing sides of the packaging, wherein the outer recesses are configured to receive a portion of the external device so as to align the external device with respect to the device mount.

2. The system according to claim 1, wherein the device mount comprises a through-opening, wherein the implantable medical device is inserted into the through-opening to fasten the implantable medical device to the device mount.

3. The system according to claim 2, wherein a circumferential inner side of the through-opening comprises a plurality of protrusions pressing against the implantable medical device so that the latter is fastened to the device mount through a press fit.

4. The system according to claim 1, wherein the packaging comprises an inner recess formed in an inner side of the packaging, wherein the device mount engages with the inner recess in a form fitting manner.

5. The system according to claim 4, wherein the packaging comprises a container and a removable lid connected to the container, wherein the inner recess is formed in the lid.

6. The system according to claim 1, wherein the implantable medical device is configured to generate a response signal in form of an ultrasound wave (U') after having performed the task and to send the response signal via the device mount to the external device, wherein the external device is configured to convert the ultrasound wave (U') into a converted signal and to send the converted signal to the programming device, wherein the programming device is configured to display reception of the converted signal and/or an information contained in the converted signal via the user interface of the programming device.

7. The system according to claim 6, wherein the task is a self-test of the implantable medical device, and wherein said information is a result of the self-test.

8. The system according to claim 1, wherein the implantable medical device is an implantable intracardiac pacemaker.

9. The system according to claim 1, wherein the programming device is provided in form of a programming device with a programming wand, where the programming device is configured to generate and send a command signal to the external device using inductive communication via the wand.

10. The system according to claim 9, wherein the external device is configured to receive the command signal in form of an inductive communication or a radio communication from the programming device and to convert the command signal into the ultrasound wave (U) and to send the ultrasound wave (U) via the device mount to the implantable medical device to trigger the implantable medical device to perform the task.

11. The system according to claim 1, wherein the programming device is configured to generate and send a command signal to the external device using radio communication.

12. A method for sending a signal to an implantable medical device using a system according to claim 1, wherein the method comprises the steps of:
   placing the external device on the portion of the packaging and applying the ultrasound wave (U) to said portion of the packaging such that the ultrasound wave (U) is passed via the device mount to the implantable medical device enclosed by the packaging.

13. The method according to claim 12, wherein the method comprises the further step of:
   generating a response signal in form of an ultrasound wave (U') with the implantable medical device and passing the response signal (U') to the external device via the device mount.

* * * * *